US010525088B2

(12) United States Patent
Kanayama et al.

(10) Patent No.: US 10,525,088 B2
(45) Date of Patent: Jan. 7, 2020

(54) LACTIC ACID BACTERIAL IMMUNOPOTENTIATING ACTIVITY-INCREASING COMPOSITION AND METHOD FOR INCREASING IMMUNOPOTENTIATING ACTIVITY OF LACTIC ACID BACTERIA

(71) Applicant: Kirin Holdings Kabushiki Kaisha, Nakano-ku, Tokyo (JP)

(72) Inventors: Masaya Kanayama, Tokyo (JP); Kyoko Tazumi, Tokyo (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/314,149

(22) PCT Filed: May 29, 2015

(86) PCT No.: PCT/JP2015/065500
§ 371 (c)(1),
(2) Date: Nov. 28, 2016

(87) PCT Pub. No.: WO2015/182735
PCT Pub. Date: Dec. 3, 2015

(65) Prior Publication Data
US 2017/0189458 A1    Jul. 6, 2017

(30) Foreign Application Priority Data

May 30, 2014 (JP) .................. 2014-113529

(51) Int. Cl.
| | | |
|---|---|---|
| A61K 35/744 | (2015.01) | |
| A61K 39/00 | (2006.01) | |
| A61K 39/39 | (2006.01) | |
| A61K 9/00 | (2006.01) | |
| A23L 33/135 | (2016.01) | |
| A61K 31/20 | (2006.01) | |
| A61K 31/047 | (2006.01) | |
| A61K 31/23 | (2006.01) | |
| A61K 31/7016 | (2006.01) | |
| A61K 31/7024 | (2006.01) | |
| A61P 37/04 | (2006.01) | |
| C12N 1/20 | (2006.01) | |
| A23L 2/52 | (2006.01) | |

(52) U.S. Cl.
CPC .............. *A61K 35/744* (2013.01); *A23L 2/52* (2013.01); *A23L 33/135* (2016.08); *A61K 9/0056* (2013.01); *A61K 9/0095* (2013.01); *A61K 31/047* (2013.01); *A61K 31/20* (2013.01); *A61K 31/23* (2013.01); *A61K 31/7016* (2013.01); *A61K 31/7024* (2013.01); *A61K 39/39* (2013.01); *A61P 37/04* (2018.01); *C12N 1/20* (2013.01); *A23V 2002/00* (2013.01); *A23Y 2240/41* (2013.01); *A61K 39/00* (2013.01); *A61K 2039/55594* (2013.01)

(58) Field of Classification Search
CPC ....... A23L 33/135; A23L 2/52; A61K 35/744; A61K 31/711; A61K 35/747; A61K 9/0053; A61K 31/047; A61K 31/20; A61K 31/7016; A61K 39/00; A61K 9/0056; A61K 9/0095; A61K 31/215; A61K 35/74; A61K 47/26; A23Y 2240/41; C12N 1/20; C12N 15/746; A23C 19/0323; A23C 19/062; A23C 9/123; A23C 9/1236; C12Q 1/6809; C12Q 1/689; C12Q 2521/301; C12R 1/01; G01N 33/6866; G01N 2469/10; G01N 33/56933; C07K 14/195; C07K 16/1253

See application file for complete search history.

(56) References Cited

U.S. PATENT DOCUMENTS

| | | |
|---|---|---|
| 5,556,785 A | 9/1996 | Kishida |
| 5,942,237 A | 8/1999 | Gizurarson et al. |
| 2011/0150952 A1* | 6/2011 | Simonnet ............... A61K 8/604 424/401 |

(Continued)

FOREIGN PATENT DOCUMENTS

| | | | |
|---|---|---|---|
| EP | 1920774 A1 | 5/2008 | |
| JP | 58020180 A * | 2/1983 | |

(Continued)

OTHER PUBLICATIONS

Chortyk et al. J. Agric. Food Chem. 44: 1551-1557, 1996, abstract.*

(Continued)

*Primary Examiner* — Sarvamangala Devi
(74) *Attorney, Agent, or Firm* — Foley & Lardner LLP

(57) ABSTRACT

It is an object of the present invention to provide a lactic acid bacterial immunopotentiating activity-increasing composition that increases the immunopotentiating activity of lactic acid bacteria having immunopotentiating activity; and a method for increasing the immunopotentiating activity of lactic acid bacteria using the composition; and a composition comprising both of lactic acid bacteria having an immunopotentiating activity and a lactic acid bacterial immunopotentiating activity-increasing composition, wherein the immunopotentiating activity of the lactic acid bacteria is increased. The present invention relates to a composition comprising lactic acid bacteria having an immunopotentiating activity and a lactic acid bacterial immunopotentiating activity-increasing composition comprising an ester compound of a polyol and a saturated fatty acid as an active ingredient.

14 Claims, 10 Drawing Sheets

(56) References Cited

U.S. PATENT DOCUMENTS

2013/0302380 A1 11/2013 Fujiwara et al.

FOREIGN PATENT DOCUMENTS

| JP | 05-097689 A | 4/1993 |
| JP | 06-206826 A | 7/1994 |
| JP | 09-508614 A | 9/1997 |
| JP | 2001-064189 A | 3/2001 |
| JP | 2001-089397 A | 4/2001 |
| JP | 2002-080364 A | 3/2002 |
| JP | 2004-222652 A | 8/2004 |
| JP | 2007-204488 A | 8/2007 |
| JP | 2007-302628 A | 11/2007 |
| JP | 2011-037888 A | 2/2011 |
| JP | 2012-184261 A | 9/2012 |
| WO | WO 2007/013613 A1 | 2/2007 |
| WO | WO 2012/091081 A1 | 7/2012 |

OTHER PUBLICATIONS

English abstract of Utena et al. JP 58020180 A, 1983.*
International Search Report and Written Opinion dated Aug. 18, 2015, in PCT/JP2015/065500.
Third party submission dated Sep. 11, 2018, in JP 2015-109271.

* cited by examiner

Lactic acid bacterial concentration: 0.1% (w/v)
A: Poem TRP-97RF (emulsifier)
B: Poem BS-20 (emulsifier)
C: Ryoto Sugar Ester P1670 (emulsifier)
D: GENU pectin (thickener polysaccharide)
E: Pectin AYD30T (thickener polysaccharide)
F: Unipectine AYD5110SB (thickener polysaccharide)

Lactic acid bacterial concentration: 0.1% (w/v)
A: Monoglycerol (Emulsy P-100)
B: Diglycerol (Poem DP-95RF)
C: Triglycerol (Poem TRP-97RF)
D: Sucrose (Ryoto Sugar Ester P1670)

Lactic acid bacterial concentration: 0.1% (w/v)
PA1: Palmitic acid (Ryoto Sugar Ester P1570)
PA2: Palmitic acid (Ryoto Sugar Ester P1670)
SA1: Stearic acid (Ryoto Sugar Ester S1570)
SA2: Stearic acid (Ryoto Sugar Ester S1670)
OA: Oleic acid (Ryoto Sugar Ester O1570)

Lactic acid bacterial concentration: 0.1% (w/v)
A: Monoglycerol myristate
B: Monoglycerol palmitate
C: Monoglycerol stearate Lactic acid bacterial concentration: 0.1% (w/v)
A: Sucrose palmitate
B: Ryoto Sugar Ester P1670

Lactic acid bacterial concentration: 0.1% (w/v)
A: No modification (Emulsy P-100)
B: Tartaric acid (Poem W-60)
C: Succinic acid (Poem B-15V)
D: Succinic acid (Poem BS-20)

Lactic acid bacterial concentration: 0.01% (w/v)
A: No modification (Emulsy P-100)
B: Tartaric acid (Poem W-60)
C: Succinic acid (Poem B-15V)
D: Succinic acid (Poem BS-20)

Lactic acid bacterial concentration: 0.01% (w/v)
Ester compound: Ryoto Sugar Ester P1670

LACTIC ACID BACTERIAL IMMUNOPOTENTIATING ACTIVITY-INCREASING COMPOSITION AND METHOD FOR INCREASING IMMUNOPOTENTIATING ACTIVITY OF LACTIC ACID BACTERIA

CROSS-REFERENCE TO RELATED APPLICATIONS

This application is a National Stage application of PCT/JP2015/065500, filed May 29, 2015, which claims priority from Japanese application JP 2014-113529, filed May 30, 2014.

TECHNICAL FIELD

The present invention relates to a lactic acid bacterial immunopotentiating activity-increasing composition that increases the immunopotentiating activity of lactic acid bacteria having immunopotentiating activity and the present invention relates to a method for increasing the immunopotentiating activity using the composition, and the present invention relates to a composition comprising both of lactic acid bacteria having immunopotentiating activity and a lactic acid bacterial immunopotentiating activity-increasing composition.

BACKGROUND ART

A cold and influenza are diseases mainly caused by infection with a virus and resulting in poor physical conditions. Experiencing the outbreak of the new influenza, people are seeking for beverages and foods having the immunopotentiating effect for preventing a cold and influenza. Lactic acid strains such as *Lactococcus lactis* subsp. *lactis* JCM5805 (see Patent Literature 1), *Lactbacillus bulgaricus* OLL1073R-1 (see Patent Literature 2), *Enterococcus faecalis* (see Patent Literature 3), *Lactobacillus brevis* subsp. *coagulans* (see Patent Literature 4), and *Lactococcus gasseri* (see Patent Literature 5) have been known to exhibit the immunopotentiating effect and used in plural beverages and foods. However, to have an adequate effect of such bacteria, an amount of the bacteria exceeding a certain amount has been required and addition of a large amount of such bacteria in a beverage has resulted in decrease in the commercial value due to, for example, production of precipitates and/or flavor deterioration. Therefore, a method for having an adequate effect of such lactic acid bacteria in a small quantity has been desired. Methods for increasing the immunopotentiating effect of lactic acid bacteria and products having an enhanced immunological effect have been reported recently. Examples include beverages and foods for increasing immunity, comprising a combination of lactic acid bacteria and cereals of a Poaceae plant (see Patent Literature 5); a composition comprising fucoidan or a fucoidan hydrolysate and an immuno-stimulating material (see Patent Literature 6); a culture obtained by lactic fermentation involving inoculating a medium containing a processed asparagus product with lactic acid bacteria (see Patent Literature 7); a method involving combined use of lactic acid bacteria and ascorbic acid (see Patent Literature 8); and a method involving combined use of lactic acid bacteria and vitamin E (see Patent Literature 9).

CITATION LIST

Patent Literature

Patent Literature 1: International Publication No. WO2012/091081
Patent Literature 2: JP Patent Publication (Kokai) No. 2011-37888 A
Patent Literature 3: JP Patent Publication (Kokai) No. 5-97689 A (1993)
Patent Literature 4: JP Patent Publication (Kokai) No. 06-206826 A (1994)
Patent Literature 5: JP Patent Publication (Kokai) No. 2012-184261 A
Patent Literature 6: International Publication No. WO2007/013613
Patent Literature 7: JP Patent Publication (Kokai) No. 2007-302628 A
Patent Literature 8: JP Patent Publication (Kokai) No. 2007-204488 A
Patent Literature 9: JP Patent Publication (Kokai) No. 2002-080364 A

SUMMARY OF INVENTION

Technical Problem

However, cereals of a Poaceae plant are a granular material and produce precipitates when used in a beverage or food. The methods using asparagus requires fermentation of a processed asparagus product with lactic acid bacteria, taking efforts and cost, as well as producing a problem of flavor. Fucoidan is a high molecular weight polysaccharide with a high viscosity and therefore difficult to handle, and a fucoidan hydrolysate is a mixture of plural oligosaccharides and produces a problem of flavor. Ascorbic acid is vulnerable to heat and vitamin E is liposoluble and difficult to handle. Moreover, the above method and the like are methods for increasing production of interferon γ and nothing is described on type I interferon, which is most important for the prevention of viral infections.

Therefore, a water-soluble ingredient that synergistically increases the immunopotentiating activity of lactic acid bacteria and has no large effect on the flavor can reduce the amount of the lactic acid bacteria to be used while maintaining its activity, and, as a result, increase the scope of the development of compositions containing the lactic acid bacteria. Compositions having a strong protective effect against viral infections can be provided by focusing on the immunopotentiating activity particularly for type I interferon.

It is an object of the present invention to provide a lactic acid bacterial immunopotentiating activity-increasing composition that increases the immunopotentiating activity of lactic acid bacteria having the immunopotentiating activity, wherein addition of a small amount of the lactic acid bacterial immunopotentiating activity-increasing composition can produce an adequate effect of the lactic acid bacteria; and a method for increasing the immunopotentiating activity of lactic acid bacteria using the composition; and a composition comprising both of lactic acid bacteria having the immunopotentiating activity and a lactic acid bacterial immunopotentiating activity-increasing composition, wherein the immunopotentiating activity of the lactic acid bacteria is increased.

Solution to Problem

The present inventors have studied diligently to achieve the aforementioned object and have found, as a result, that ester compounds of a polyol and a saturated fatty acid have an effect of enhancing the immunopotentiating activity of lactic acid bacteria, thereby completing the present invention.

More specifically, the present invention is as follows:
[1] A composition comprising lactic acid bacteria having immunopotentiating activity and a lactic acid bacterial immunopotentiating activity-increasing composition comprising an ester compound of a polyol and a saturated fatty acid as an active ingredient.
[2] The composition according to [1], wherein the immunopotentiating activity of the lactic acid bacteria having immunopotentiating activity is increased.
[3] The composition according to [1] or [2], wherein the composition is a beverage or food.
[4] The composition according to any one of [1] to [3], wherein the polyol is selected from the group consisting of monoglycerol, polyglycerol, and sucrose,
[5] The composition according to any one of [1] to [4], wherein the saturated fatty acid is selected from the group consisting of caprylic acid, capric acid, lauric acid, myristic acid, palmitic acid, stearic acid and behenic acid.
[6] The composition according to any one of [1] to [5], wherein the ester compound of a polyol and a saturated fatty acid is not modified with any organic acid.
[7] The composition according to any one of [1] to [6], wherein the ratio of the concentration of the ester compound of a polyol and a saturated fatty acid to the concentration of the lactic acid bacteria having immunopotentiating activity is in the range of 0.5 to 50:1.
[8] The composition according to any one of [1] to [7], wherein the lactic acid bacteria having immunopotentiating activity is lactic acid bacteria capable of inducing interferon production of an interferon-producing cell,
[9] The composition according to any one of [1] to [8], wherein the lactic acid bacteria having immunopotentiating activity is selected from the group consisting of *Lactococcus garvieae*, *Lactococcus lactis* subsp. *cremoris*, *Lactococcus lactis* subsp. *lactis*, *Lactococcus lactis* subsp. *hordniae*, *Leuconostoc lactis*, *Pediococcus damnosus*, *Streptococcus thermophilus*, *Lactobacillus brevis* subsp. *coagulans*, and *Enterococcus faecalis*.
[10] The composition according to [8] or [9], wherein the lactic acid bacteria having immunopotentiating activity is *Lactococcus lactis* JCM5805.
[11] A method for increasing immunopotentiating activity of lactic acid bacteria having immunopotentiating activity, comprising contacting lactic acid bacteria having immunopotentiating activity and a lactic acid bacterial immunopotentiating activity-increasing composition comprising an ester compound of a polyol and a saturated fatty acid as an active ingredient.
[12] The method according to [11], wherein the polyol is selected from the group consisting of monoglycerol, polyglycerol, and sucrose.
[13] The method according to [11] or [12], wherein the saturated fatty acid is selected from the group consisting of caprylic acid, capric acid, lauric acid, myristic acid, palmitic acid, stearic acid, and behenic acid.
[14] The method according to any one of [11] to [13], wherein the ester compound of a polyol and a saturated fatty acid is not modified with any organic acid.
[15] The method according to any one of [11] to [14], wherein the ratio of the concentration of the ester compound of a polyol and a saturated fatty acid to the concentration of the lactic acid bacteria having immunopotentiating activity is in the range of 0.5 to 50:1.
[16] The method according to any one of [11] to [15], wherein the lactic acid bacteria having immunopotentiating activity is lactic acid bacteria capable of inducing interferon production of an interferon-producing cell.
[17] The method according to any one of [11] to [16], wherein the lactic acid bacteria having immunopotentiating activity is selected from the group consisting of *Lactococcus garvieae*, *Lactococcus lactis* subsp. *cremoris*, *Lactococcus lactis* subsp. *lactis*, *Lactococcus lactis* subsp. *hordniae*, *Leuconostoc lactis*, *Pediococcus damnosus*, *Streptococcus thermophilus*, *Lactobacillus brevis* subsp. *coagulans*, and *Enterococcus faecalis*.
[18] The method according to [16] or [17], wherein the lactic acid bacteria having immunopotentiating activity is *Lactococcus lactis* JCM5805.

The description of the present application encompasses the contents stated in the description and/or drawings of JP Patent Application No. 2014-113529, which the priority of the present application is based on.

Advantageous Effects of Invention

Ester compounds of a polyol and a saturated fatty acid increase the immunopotentiating activity of lactic acid bacteria having immunopotentiating activity. Accordingly, coexistence of lactic acid bacteria with an ester compound of a polyol and a saturated fatty acid, for example, in culture increases the effect of the lactic acid bacteria on interferon-producing cells to induce the interferon production. By using a lactic acid bacterial immunopotentiating activity-increasing composition comprising an ester compound of a polyol and a saturated fatty acid as an active ingredient, the immunopotentiating activity of the lactic acid bacteria can be increased. Moreover, by adding a lactic acid bacterial immunopotentiating activity-increasing composition into a composition such as a beverage or food containing lactic acid bacteria, the immunopotentiating activity of the lactic acid bacteria in the beverage or food can be increased. The immunopotentiating activity of lactic acid bacteria is increased by a lactic acid bacterial immunopotentiating activity-increasing composition comprising an ester compound of a polyol and a saturated fatty acid as an active ingredient and therefore even a small amount of lactic acid bacteria contained in a composition such as a beverage or food can provide a marked immunopotentiating effect.

DESCRIPTION OF EMBODIMENTS

Figure 1:
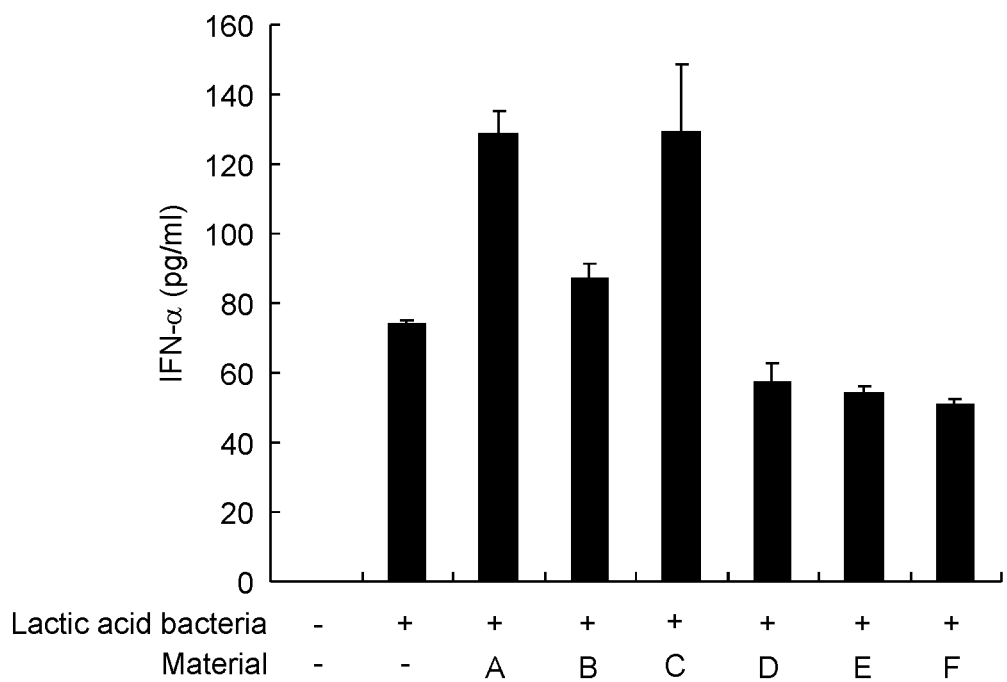
FIG. 1 illustrates the results of screening for immunopotentiating activity increasing compositions.

The present invention will be described in detail below.

The present invention relates to lactic acid bacterial immunopotentiating activity-increasing compositions that increase the immunopotentiating activity of lactic acid bacteria. The compositions comprise an ester compound of a polyol and a saturated fatty acid as an active ingredient, wherein the ester compound has a structure consisting of a hydrophilic moiety and a lipophilic moiety in which the hydrophilic moiety is bonded to the lipophilic moiety by an ester bond, wherein the hydrophilic moiety is a polyol and the lipophilic moiety is a saturated fatty acid.

The polyol in the ester compound of a polyol and a saturated fatty acid is an alcohol having 2 or more hydroxyl groups in the molecule, wherein the number of hydroxyl groups is, for example, 2 to 15, but not limited. The polyol may have an aldehyde group and/or a ketone group. A polyol having an aldehyde group and/or a ketone group is sugar or a sugar alcohol.

The number of carbon atoms in the polyol contained in a lactic acid bacterial immunopotentiating activity-increasing composition according to the present invention is 2 to 20 and preferably 3 to 20. The greater molecular weight is preferred for the polyol and the molecular weight is 50 or more, preferably 60 or more, and more preferably 90 or more. In the comparison of the increasing effect of, for example, sucrose (molecular weight 342), triglycerol (molecular weight 240), diglycerol (molecular weight 166), and monoglycerol (molecular weight 92), the effect is greater in this order.

Examples of the polyol include ethylene glycol ($C_2H_6O_2$) and propylene glycol ($C_3H_8O_2$),) which are dihydric alcohol; glycerol ($C_3H_8O_3$), which is trihydric alcohol; diethylene glycol ($C_4H_{10}O_3$)), which is tetrahydric alcohol; diglycerol ($C_6H_{14}O_5$), which is a pentahydric alcohol; triglycerol ($C_9H_{20}O_7$); and polyglycerol. Polyethyleneglycol, which has a large number of hydroxyl groups, may be also used. Examples of the polyol that is sugar include sucrose ($C_{12}H_{22}O_{11}$). Examples of the polyol that is a sugar alcohol include xylitol ($C_5H_{12}O_5$), sorbitol ($C_6H_{14}O_6$), mannitol ($C_6H_{14}O_6$), and sorbitan.

When an organic acid such as succinic acid or tartaric acid is bonded to the polyol, the immunopotentiating activity-increasing effect of the lactic acid bacteria is decreased. Polyols bonded with an organic acid, however, have the detectable immunopotentiating activity-increasing effect and can therefore be used. Polyols bonded with no organic acid are preferably used.

The number of carbon atoms in a saturated fatty acid contained in a lactic acid bacterial immunopotentiating activity-increasing composition of the present invention is 8 to 30. More specifically, examples include caprylic acid (octanoic acid) (C8), capric acid (decanoic acid) (C10), lauric acid (dodecanoic acid) (C12), myristic acid (tetradecanoic acid) (C14), pentadecylic acid (pentadecanoic acid) (C15), palmitic acid (hexadecanoic acid) (C16), margaric acid (heptadecanoic acid) (C17), stearic acid (octadecanoic acid) (C18), arachidic acid (icosanoic acid) (C20), behenic acid (docosanoic acid) (C22), lignoceric acid (tetradocosanoic acid) (C24), cerotic acid (hexadocosanoic acid) (C26), montanic acid (octadocosanoic acid) (C26), and melissic acid (C28). Among these, caprylic acid, capric acid, lauric acid, myristic acid, palmitic acid, stearic acid, and behenic acid may be preferably used.

A lactic acid bacterial immunopotentiating activity-increasing composition of the present invention is a composition comprising the ester compound in which a hydroxyl group of the polyol is bonded with a carboxyl group of the saturated fatty acid(s) by ester bonding as an active ingredient.

The number of the saturated fatty acid(s) bonded to 1 molecule of the polyol in the ester compound of a polyol and a saturated fatty acid(s) is not limited, and the saturated fatty acid(s) may be bonded to only one hydroxyl group. The saturated fatty acid(s) may be bonded to plural hydroxyl groups, but not all hydroxyl groups. Examples include monoesters, in which 1 fatty acid is attached to a polyol, diesters, in which 2 fatty acids are attached to a polyol, and triesters, in which 3 fatty acids are attached to a polyol. In an ester compound in which plural saturated fatty acids are bonded to one molecule of a polyol, the plural saturated fatty acids may be the same type of saturated fatty acids or different types of saturated fatty acids may be bonded.

The compositions comprising an ester compound of a polyol and a saturated fatty acid as an active ingredient comprise 45 (w/v) % or more, preferably 50 (w/v) % or more, more preferably 60 (w/v) % or more, more preferably 70 (w/v) % or more, more preferably 80 (w/v) % or more, more preferably 90 (w/v) % or more, and particularly preferably 95 (w/v) % or more of the ester compound of a polyol and a saturated fatty acid and may comprise 100 (w/v) % of the ester compound.

Examples of the ester compound include fatty acid esters of glycerol (monoglyceride), fatty acid esters of polyglycerol such as fatty acid esters of diglycerol and fatty acid esters of triglycerol, fatty acid esters of propylene glycol, fatty acid esters of sorbitan, and fatty acid esters of sucrose. More specifically, examples include glycerol caprylate, glycerol caprate, glycerol laurate, glycerol myristate, glycerol palmitate, glycerol stearate, glycerol behenate, diglycerol caprylate, diglycerol caprate, diglycerol laurate, diglycerol myristate, diglycerol palmitate, diglycerol stearate, diglycerol behenate, triglycerol caprylate, triglycerol caprate, triglycerol laurate, triglycerol myristate, triglycerol palmitate, triglycerol stearate, triglycerol behenate, tetraglycerol caprylate, tetraglycerol caprate, tetraglycerol laurate, tetraglycerol myristate, tetraglycerol palmitate, tetraglycerol stearate, tetraglycerol behenate, decaglycerol caprylate, glycerol caprate, glycerol laurate, decaglycerol myristate, decaglycerol palmitate, decaglycerol stearate, decaglycerol behenate, sucrose caprylate, sucrose caprate, sucrose laurate, sucrose myristate, sucrose palmitate, sucrose stearate, and sucrose behenate.

The ester compound of a polyol and a saturated fatty acid or a composition comprising the ester compound serves as a surfactant and may also be referred to as an ester-type non-ionic surfactant or a polyol-type surfactant. The ester compound of a polyol and a saturated fatty acid or a composition comprising the ester compound serves as an emulsifier and commercially available emulsifiers can be used.

Examples of emulsifiers containing such an ester compound of a polyol and a saturated fatty acid include the following. In the following description, types of ester compounds are listed in the parentheses after the trade names of emulsifiers and the emulsifier contains the ester compound in the parenthesis most. The content (w/v)) of the ester compound is 45% or more, preferably 80% or more, more preferably 85% or more, more preferably 90% or more, and more preferably 95% or more.

Ester compounds of a fatty acid and glycerol include food emulsifiers such as Emulsy P-100 (monoglycerol palmitate and monoglycerol stearate), Poem M-100 (glycerol monocaprylate), Poem M-200 (glycerol monocaprate), Poem M-300 (glycerol monolaurate), Poem V-100 (glycerol monostearate), Rikemal B-100 (glycerol monobehenate), Poem V-200 (glycerol mono/distearate), Poem B-200 (glycerol mono/dibehenate), Poem DL-100 (diglycerol monolaurate), Poem DM-100 (diglycerol monomyristate), Poem DS-100A (diglycerol monostearate), Poem DP-95RF (diglycerol palmitate), Rikemal L-71-D (diglycerol laurate), Rikemal S-71-D (diglycerol stearate), Poem TRP-97RF (triglycerol monopalmitate), Poem J-4081V (tetraglycerol stearate), Poem J-0021 (decaglycerol laurate), and Poem J-0081HV (decaglycerol stearate) (all from Riken Vitamin Co., Ltd.), which are fatty acid esters of glycerol or fatty acid esters of polyglycerol.

Examples of the ester compounds of a fatty acid and propylene glycol include food emulsifiers such as Rikemal PL-100 (propylene glycol monolaurate), Rikemal PP-100 (propylene glycol monopalmitate), Rikemal PS-100 (propylene glycol monostearate), and Rikemal PB-100 (propylene glycol monobehenate) (all from Riken Vitamin Co., Ltd.).

Examples of ester compounds of a fatty acid and sorbitan include food emulsifiers such as Rikemal L-250A (sorbitan laurate), Rikemal P-300 (sorbitan palmitate), Poem S-60V (sorbitan stearate), Poem S-65V (sorbitan tristearate), Rikemal B-150 (sorbitan tribehenate), Rikemal C-250 (sorbitan caprate) (all from Riken Vitamin Co., Ltd.).

Examples of ester compounds of a fatty acid and sucrose include food emulsifiers such as Ryoto (registered trademark) Sugar Ester S-1570, S-1670 (sucrose stearate), Ryoto (registered trademark) Sugar Ester P-1570, P-1670 (sucrose palmitate), Ryoto (registered trademark) Sugar Ester M-1695 (sucrose myristate), Ryoto (registered trademark) Sugar Ester P-1695 (sucrose laurate), Ryoto (registered trademark) Sugar Ester B-370 (sucrose behenate) (all from Mitsubishi-Kagaku Foods Corporation).

Examples of food emulsifiers in which an organic acid is bonded to a polyol include Poem W-60 (diacetyltartaric fatty acid monoglyceride), Poem B-15V and Poem BS-20 (succinic fatty acid monoglyceride), and Poem K-30 (citric fatty acid monoglyceride) (all from Riken Vitamin Co., Ltd.).

Lactic acid bacteria of which immunopotentiating activity is increased by a lactic acid bacterial immunopotentiating activity-increasing composition according to the present invention are lactic acid bacteria that intrinsically have the immunopotentiating activity even in the absence of the composition according to the present invention. The phrase "have immunopotentiating activity" means that the lactic acid bacteria has the effect on immunocompetent cells that are interferon-producing cells and promote their interferon production in vivo and in vitro. The immunopotentiating activity may be also referred to as interferon production-inducing activity. The immunocompetent cells include spleenocytes and myeloblasts. Particular examples of the immunocompetent cells include plasmacytoid dendritic cells (pDCs).

Interferons include Type I interferons, Type II interferons, and Type III interferons. Type I interferons are cytokines considered to be effective against viral infections and include interferon-α (1, 2, 4, 5, 6, 7, 8, 10, 13, 14, 16, 17, 21) and interferon-β. Type II interferons include interferon-γ and Type III interferons include interferon-λ. In particular, lactic acid bacteria having the inducibility of the production of Type I and Type III interferons and particularly the inducibility of the production of interferon-α, a Type I interferon, are preferred.

Furthermore, smaller lactic acid bacteria are preferred among lactic acid bacteria. Examples include lactic acid bacteria having a cell diameter of 5 μm or less, preferably 2 μm or less, and more preferably 1 μm or less.

Examples of lactic acid bacteria having the inducibility of the interferon production include lactic acid cocci of the genus *Lactococcus*, the genus *Leuconostoc*, the genus *Pediococcus*, the genus *Streptococcus*, the genus *Lactobacillus*, and the genus *Enterococcus*.

Such lactic acid bacteria include, but are not limited to, lactic acid bacteria that can promote the interferon production from plasmacytoid dendritic cells (pDCs).

Examples of the lactic acid bacteria that can activate plasmacytoid dendritic cells (pDCs) and promote the interferon production from pDCs include preferably lactic acid cocci, and more preferably, those in the genus *Lactococcus*, the genus *Leuconostoc*, the genus *Pediococcus*, and the genus *Streptococcus*. More particularly, examples include *Lactococcus garvieae, Lactococcus lactis* subsp. *cremoris, Lactococcus lactis* subsp. *lactis, Lactococcus lactis* subsp. *hordniae, Leuconostoc lactis, Pediococcus damnosus,* and *Streptococcus thermophilus*. When plasmacytoid dendritic cells are activated by lactic acid bacteria, cell projections characteristic of activated dendritic cells appear and the cells produce Type I and Type III interferons.

Specific examples of such lactic acid bacterial strains include *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, *Streptococcus thermophilus* TA-45. Among these, *Lactococcus lactis* subsp. *lactis* JCM5805 and *Lactococcus lactis* subsp. *lactis* JCM20101, which have a particularly high inducibility of the interferon-α production, and particularly *Lactococcus lactis* JCM5805 may be preferably used.

Examples of lactic acid bacteria in the genus *Lactobacillus* include *Lactobacillus brevis* subsp. *coagulans* (JP Patent Publication (Kokai) No. 6-206826 A (1994)) and examples of specific strains include *Lactobacillus brevis* subsp. *Coagulans* KB290. Examples of lactic acid bacteria in the genus *Enterococcus* include *Enterococcus faecalis* and examples of specific strains include *Enterococcus faecalis* NF-1011, *Enterococcus faecalis* FK-23, and *Enterococcus faecalis* NT.

Furthermore, lactic acid bacteria having the interferon-inducing activity to the living body even when orally administered is preferred for increasing the immunopotentiating activity of the lactic acid bacteria with an immunopotentiating activity-increasing composition of the present invention. The aforementioned *Lactococcus lactis* JCM5805 can exhibit a high INF production-inducing activity to the living body also when administered orally.

Furthermore, bacterial strains equivalent with *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, *Streptococcus thermophilus* TA-45, *Lactobacillus brevis* subsp. *Coagulans* KB290, *Enterococcus faecalis* NF-1011, *Enterococcus faecalis* FK-23, *Enterococcus faecalis* NT can be used. The term "strains equivalent" refers to strains derived from the aforementioned strains or strains which the aforementioned strains are derived from or progeny strains thereof. The equivalent strains may be stored in other strain preservation organization.

The immunopotentiating activity of the aforementioned lactic acid bacteria can be increased by adding a lactic acid bacterial immunopotentiating activity-increasing composition according to the present invention to the aforementioned lactic acid bacteria.

A lactic acid bacterial immunopotentiating activity-increasing composition according to the present invention may be used at such a concentration that the ratio of the concentration of the composition to the concentration of the lactic acid bacteria is 0.5 to 50:1. The concentration of lactic acid bacteria may be expressed as the weight of the lactic acid bacteria (dry weight)/the volume of liquid containing the lactic acid bacteria (w/v)) and the weight of the lactic acid bacteria may be measured after centrifuging the lactic acid bacteria suspension to precipitate the lactic acid bacteria and drying the precipitation. For example, 0.01 to 0.1 (w/v) % of lactic acid bacteria and 0.005 to 5 (w/v) % of the lactic acid bacterial immunopotentiating activity-increasing composition may be mixed. In this mixing, the amount of the lactic acid bacterial immunopotentiating activity-increasing composition may be preferably changed according to the concentration range of the lactic acid bacteria. For example, if the lactic acid bacterial concentration is 0.01 (w/v) %, then 0.05 to 0.5 (w/v) % of the lactic acid bacterial immunopotentiating activity-increasing composition may be added to 0.01 (w/v) % of the lactic acid bacteria (the ratio of the concentration of the lactic acid bacterial immunopotentiating activity-increasing composition concentration to the lactic acid bacterial concentration is 5 to 50:1) and if the lactic acid bacterial concentration is 0.1 (w/v) %, then 0.05 to 0.5 (w/v) % of the lactic acid bacterial immunopotentiating activity-increasing composition may be added to 0.1 (w/v) % of the lactic acid bacteria (the ratio of the concentration of the lactic acid bacterial immunopotentiating activity-increasing composition to the lactic acid bacterial concentration is 0.5 to 5:1). Lactic acid bacterial immunopotentiating activity-inversing agents according to the present invention can increase the immunopotentiating activity of lactic acid bacteria at low lactic acid bacterial concentrations of 0.01 to 0.1 (w/v) % and immunopotentiating activity greater than that of 0.1 (w/v) % of the lactic acid bacteria to which no lactic acid bacterial immunopotentiating activity-increasing composition is added can be obtained by the addition of 0.05 to 0.5 (w/v) % of the lactic acid bacterial immunopotentiating activity-increasing composition to 0.01 (w/v) % of lactic acid bacteria.

The immunopotentiating activity of a small amount of lactic acid bacteria can be thus increased by a lactic acid bacterial immunopotentiating activity-increasing composition according to the present invention. As a result, an equivalent immunopotentiating effect can be obtained with a smaller amount of the lactic acid bacteria, relative to the immunopotentiating effect obtained by using lactic acid bacteria whose immunopotentiating activity is not increased by the lactic acid bacterial immunopotentiating activity-increasing composition according to the present invention.

The immunopotentiating activity of lactic acid bacteria is increased by the lactic acid bacterial immunopotentiating activity-increasing composition according to the present invention. The immunopotentiating activity of lactic acid bacteria can be increased by contacting the lactic acid bacteria with a lactic acid bacterial immunopotentiating activity-increasing composition according to the present invention. In order to contacting lactic acid bacteria with a lactic acid bacterial immunopotentiating activity-increasing composition, the lactic acid bacteria may be cultured in the presence of the lactic acid bacterial immunopotentiating activity-increasing composition or the lactic acid bacterial immunopotentiating activity-increasing composition may be added to a liquid containing the lactic acid bacteria. Both of the lactic acid bacteria and the lactic acid bacterial immunopotentiating activity-increasing composition may be also contained in a composition and may be stored in this condition at room temperature or by refrigeration or freezing.

The lactic acid bacteria whose immunopotentiating activity is increased acts on immunocompetent cells that are INF-producing cells contained in intestinal cells, myeloblasts, or spleenocytes and promotes the interferon production of the cells. As a result, the production of any of Type I interferons, Type II interferons, and Type III interferons may be promoted. Particularly, the production of Type I interferons and, more particularly, that of interferon-$\alpha$ are promoted. The production of Type II interferons such as interferon-$\gamma$ from natural killer and Th1 cells can be also promoted with a lactic acid bacterial immunopotentiating activity-increasing composition according to the present invention. The promotion of the interferon production increases the immune activity in the living body. Lactic acid bacterial immunopotentiating activity-increasing compositions according the present invention can promote the production of both of Type I and Type III interferons simultaneously, that is, they can promote the production of interferon-$\alpha$, interferon-$\beta$, and interferon-$\lambda$. simultaneously. Furthermore, lactic acid bacterial immunopotentiating activity-increasing compositions according to the present invention can activate plasmacytoid dendritic cells (pDCs). When plasmacytoid dendritic cells are activated, cell projections characteristic of activated dendritic cells appear and the cells produce Type I and Type III interferons.

Whether the immunopotentiating activity of lactic acid bacteria is increased by a lactic acid bacterial immunopotentiating activity-increasing composition according to the present invention can be determined by mixing the lactic acid bacteria and immunocompetent cells that are interferon-producing cells, culturing the cells in the presence of a lactic acid bacterial immunopotentiating activity-increasing composition according to the present invention, and measuring the interferon production from the immunocompetent cells to determine whether it has been promoted in comparison with that without the addition of the lactic acid bacterial immunopotentiating activity-increasing composition. The increase of the interferon production may be evaluated by measuring the amount of interferon in the culture medium by ELISA. When the immunopotentiating activity of lactic acid bacteria is increased by a lactic acid bacterial immunopotentiating activity-increasing composition according to the present invention, the amount of the production of interferon-α from interferon-producing cells is increased by 10% or more, preferably 20% or more, more preferably 40% or more, or most preferably 80% or more by the lactic acid bacteria whose immunopotentiating activity is increased. The degree of the increase may be indicated, for example, by the concentration of interferon-α in the lactic acid bacterial medium when the amount of interferon-α produced is measured in vitro.

Lactic acid bacteria whose immunopotentiating activity is increased by a lactic acid bacterial immunopotentiating activity-increasing composition according to the present invention may be used as a medicine for inducing the production of interferon and increasing the immune activity in the living body. That is, the lactic acid bacteria whose immunopotentiating activity is increased by the lactic acid bacterial immunopotentiating activity-increasing composition may be used as an immunoadjuvant or an immunopotentiating agent. Such a medicine may be used a prophylactic or therapeutic agent for cancers including kidney cancer, multiple myeloma, chronic myelogenous leukemia, hairy cell leukemia, glioblastoma, medulloblastoma, astrocytoma, malignant melanoma, mycosis fungoides, and adult T cell-leukemia; viral infections including subacute sclerosing panencephalitis, HTLV-1 myelopathy, hepatitis B, and hepatitis C; bacterial infections such as *Chlamydia* (venereal disease), *Mycobacteria* (tuberculosis), *Listeria* (sepsis), *Staphylococcus* (food poisoning), and *Helicobacter* (gastritis); and autoimmune diseases including multiple sclerosis, which have been already known as adaptation diseases of Type I interferons. The medicine is particularly useful as preventive and therapeutic agents against viral infections. The medicine may be used as a prophylactic or therapeutic agent for osteoporosis since Type I interferons are known to have the function of inhibiting differentiation from osteoblasts to osteoclasts as their activity.

Furthermore, the lactic acid strain whose immunopotentiating activity is increased by a lactic acid bacterial immunopotentiating activity-increasing composition according to the present invention may be used as vaccine by expressing an antigen corresponding to a certain disease in the strain using a genetic technique. Such a xenogeneic antigen-expressing strain is particularly suitable as a host for the oral vaccine since the cell wall of lactic acid bacteria serves to protect the antigen from gastric acid. Vaccines generally include live vaccines, inactivated whole virion vaccines, and split vaccines. However, live vaccines has a risk of reversion to pathogenic viruses, inactivated whole virion vaccines may cause side effects of impurities, and split vaccines, which are the safest, have problems of efficacy. To overcome such problems, recombinant vaccines expressing only the antigen of interest have been developed. The expression of antigen in lactic acid bacteria whose immunopotentiating activity is increased by a lactic acid bacterial immunopotentiating activity-increasing composition according to the present invention would produce the adjuvant effect as well and be very useful.

The form of the lactic acid bacteria whose immunopotentiating activity is increased by a lactic acid bacterial immunopotentiating activity-increasing composition according to the present invention is not particularly limited. Examples include powder, granules, tablets, syrups, injections, drops, powdered drugs, suppositories, suspensions, and ointments. Pharmaceutical compositions according to the present invention may be orally administered or may be parenterally administered, such as by intravenous injection, intramuscular injection, subcutaneous administration, rectal administration, or transdermal administration, but oral administration is preferred. The aforementioned interferon production-inducing agent may contain an excipient, a disintegrator, a binder, a lubricant, and/or a colorant. Examples of the excipient include glucose, lactose, cornstarch, and Sorbit. Examples of the disintegrator include starch, sodium alginate, gelatin powder, calcium carbonate, calcium citrate, and dextrin. Examples of the binder include dimethylcellulose, polyvinyl alcohol, polyvinyl ether, methylcellulose, ethyl cellulose, Arabian gum, gelatin, hydroxypropyl cellulose, and polyvinylpyrrolidone. Examples of lubricants include talc, magnesium stearate, polyethyleneglycol, and hydrogenated vegetable oils. The dose may be determined as appropriate according to age, body weight, sex of the patient receiving administration, difference of disease, and degrees of symptoms and administered once a day or several divided doses may be administered daily. An amount of culture corresponding to $1\times10^9$ to $1\times10^{12}$ cells per dose may be administered. Alternatively, 1-1000 mg in terms of the weight of lactic acid bacterial cells per dose may be administered.

Furthermore, the lactic acid bacteria whose immunopotentiating activity is increased by a lactic acid bacterial immunopotentiating activity-increasing composition according to the present invention may be used in a beverage or food. The inclusion of the lactic acid bacteria in a beverage or food allows use of the beverage or food as a beverage or food for inducing the interferon production, an immunopotentiating beverage or food, an immunostimulatory beverage or food or a beverage or food for preventing viral infection. Examples of the beverages and foods for the purpose include milk and dairy products; beverages, seasonings; alcoholic beverages; processed agricultural and forest foods; confectioneries and breads; grain flours and noodles; processed marine products; processed live stock products; oils and fats and processed oils and fats; frozen cooked foods; retort foods; instant foods, and food materials. In particular, the lactic acid bacteria can be used in fermenting dairy products such as yogurts and cheeses and lactic fermenting beverages. When used in a fermenting beverage or food, a required amount of lactic acid bacteria having immunopotentiating activity may be added to the fermenting beverage or food as a dead bacteria or may be used as lactic acid bacteria starter to produce a fermenting beverage or food.

Beverages and foods according to the present invention include health beverages and foods, beverages and foods for specific health uses, functional nutritional beverages and foods, and beverage or food supplements. As used herein, the term "beverages and foods for specified health uses" refers to beverages and foods that are taken for a specific health purpose in diets and have an indication that the health purpose may be achieved by the intake. These beverages and foods may have an indication, for example, that it increases the immune function of the body; activates the function of the immune function of the body; reduces the possibility of catching a cold; reduces the possibility of being infected with viruses such as influenza virus, norovirus, or rotavirus; or has a cancer-preventing effect.

Furthermore, a lactic acid bacterial immunopotentiating activity-increasing composition according to the present invention may be added to a beverage or food containing lactic acid bacteria. The immunopotentiating activity of the lactic acid bacteria contained in the beverage or food is increased by a lactic acid bacterial immunopotentiating activity-increasing composition and the function of the beverage or food is further improved.

The present invention comprises a composition containing both of lactic acid bacteria and a lactic acid bacterial immunopotentiating activity-increasing composition according to the present invention. The composition includes beverages and foods and pharmaceuticals.

A composition containing both of lactic acid bacteria and a lactic acid bacterial immunopotentiating activity-increasing composition may contain them such that the ratio of the concentration of the lactic acid bacteria and the concentration of the lactic acid bacterial immunopotentiating activity-increasing composition is 0.5 to 50:1. For example, 0.01 to 0.1 (w/v) % of lactic acid bacteria and 0.05 to 5 (w/v) % of a lactic acid bacterial immunopotentiating activity-increasing composition may be mixed. In this mixing, the amount of the lactic acid bacterial immunopotentiating activity-increasing composition may be preferably changed according to the concentration range of the lactic acid bacteria. For example, if the lactic acid bacterial concentration is 0.01 (w/v) %, then 0.05 to 0.5 (w/v) % of the lactic acid bacterial immunopotentiating activity-increasing composition may be added to 0.01 (w/v) % of the lactic acid bacteria (the ratio of the concentration of the lactic acid bacterial immunopotentiating activity-increasing composition concentration to the lactic acid bacterial concentration is 5 to 50:1) and if the lactic acid bacterial concentration is 0.1 (w/v) %, then 0.05 to 0.5 (w/v) % of the lactic acid bacterial immunopotentiating activity-increasing composition may be added to 0.1 (w/v) % of the lactic acid bacteria (the ratio of the concentration of the lactic acid bacterial immunopotentiating activity-increasing composition to the lactic acid bacterial concentration is 0.5 to 5:1).

EXAMPLES

The present invention will be specifically described by the following Examples, but the present invention is not limited by these Examples.

Example 1 Screening for Immunopotentiating Activity-Increasing Agent

Method

Spleenocytes were collected from female 129/SV mice according to a usual method and erythrocytes were removed. The obtained spleenocytes were suspended at $4 \times 10^6$ cells/ml in RPMI medium (Sigma-Aldrich Co. LLC) containing 10% FBS and 50 μM β-mercaptoethanol. To 500 μl of the obtained cell suspension, 5 μl of a mixture of lactic acid bacteria (the strain JCM5805) and one of the samples (materials) indicated in FIG. 1 was added. The resulting mixtures were cultured at 37° C., 5% $CO_2$ in a $CO_2$ incubator. The mixtures of the lactic acid bacteria and one of the samples indicated in the figure contained 0.1 (w/v) % of the lactic acid bacteria and 0.25 (w/v) % of one of the samples. Culture supernatants were collected 24 hours later and the concentration of interferon-α was measured by interferon-α assay kit (Pestka Biomedical Laboratories, Inc).

Result

Results are illustrated in FIG. 1. JCM5805 exhibited the interferon-α inducing activity alone and the interferon-α inducing activity was synergistically increased by Poem TRP-97RF (triglycerol monopalmitate), Ryoto Sugar Ester P1670 (sucrose palmitate), and Poem BS-20 (succinic and fatty acid esters of monoglyceride), which are compositions containing an ester compound of a polyol and a fatty acid used as an emulsifier, while polysaccharides (GENU pectin, Pectin AYD30T, Unipectine AYD5110SB) did not increase the interferon-α inducing activity. The results revealed that the immunopotentiating activity of the strain JCM5805 is increased by ester compounds of a polyol and a fatty acid, which are used as an emulsifier.

Example 2 Narrowing Examination of Type (Hydrophilic Moiety) of Ester Compound of Polyol and Fatty Acid Ester compounds of a polyol and a fatty acid are substances that serve to homogenize substances that do not mix, such as water and oil, on the interface between the substances and consist of a hydrophilic moiety and a hydrophobic moiety. Products modified with an organic acid may be used depending on the application. To narrow the range of ester compounds of a polyol and a fatty acid that increase the immunopotentiating activity of lactic acid bacteria, examination of the polyol, the hydrophilic moiety, was conducted first.

Method

Figure 2:
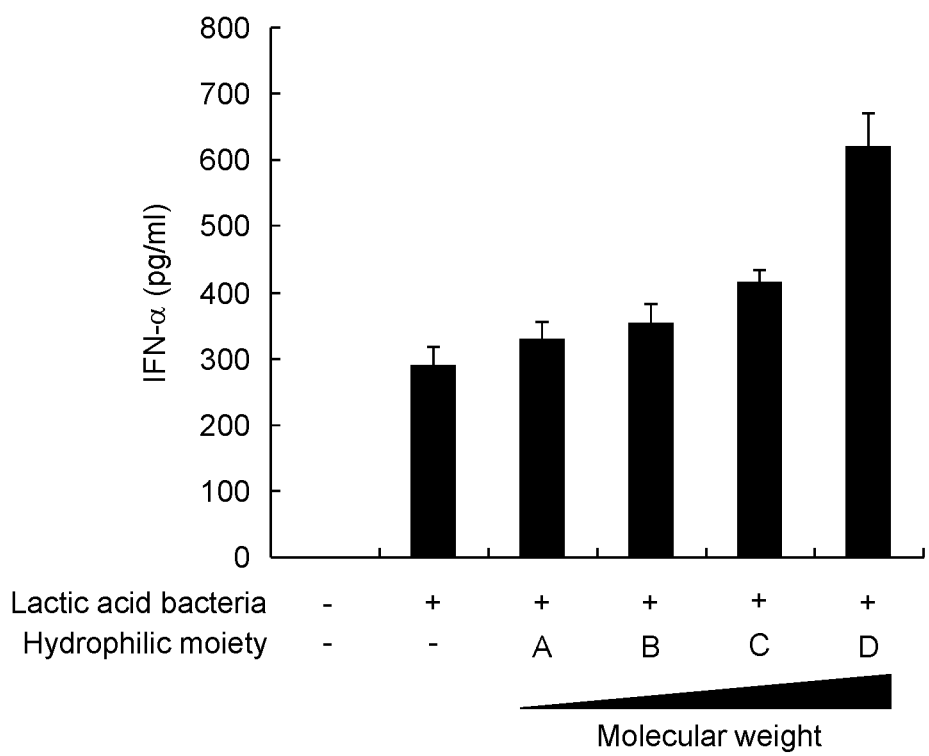
FIG. 2 illustrates the results of a narrowing examination of the type (the hydrophilic moiety) of ester compounds of a polyol and a fatty acid.

To 500 μl of the cell suspension prepared by the method described in Example 1, 5 μl of a mixture of the lactic acid bacteria (the strain JCM5805) and one of the samples indicated in FIG. 2 was added. The resulting mixtures were cultured at 37° C., 5% $CO_2$ in a $CO_2$ incubator. The mixtures of the lactic acid bacteria and one of the samples indicated in the figure contained 0.1 (w/v) % of the lactic acid bacteria and 0.25 (w/v) % of one of the samples. The samples were the lactic acid bacteria only, Emulsy P-100 (mainly containing an ester compound of monoglycerol and a saturated fatty acid) (A) (Riken Vitamin Co., Ltd.), Poem DP-95RF (mainly containing an ester compound of diglycerol and a saturated fatty acid) (B) (Riken Vitamin Co., Ltd.), Poem TRP-97RF (mainly containing an ester compound of triglycerol and a saturated fatty acid) (C) (Riken Vitamin Co., Ltd.), and Ryoto Sugar Ester P-1670 (mainly containing an ester compound of sucrose and a saturated fatty acid) (D) (Mitsubishi-Kagaku Foods Corporation). Culture supernatants were collected 24 hours later and the concentration of interferon-α was measured by interferon-α assay kit (Pestka Biomedical Laboratories, Inc). Accordingly, the fatty acid, the hydrophilic moiety, was examined by using ester compounds containing a saturated fatty acid as the unified hydrophobic moiety and a variety of polyols: monoglycerol, diglycerol, triglycerol, and sucrose as the hydrophilic moiety.

Result

Results are illustrated in FIG. 2. 0.1% JCM5805 alone exhibits the interferon-α inducing activity and the interferon-α inducing activity was further increased by both types of ester compounds. Accordingly, it was found that a wide variety of polyols can be used as the hydrophilic moiety of an ester compound to increase the immunopotentiating activity of lactic acid bacteria.

Moreover, polyols having a higher molecular weight had higher effects.

Example 3 Narrowing Examination of Type (Hydrophobic Moiety) of Ester Compound of Polyol and Fatty Acid Polyols were found to be available as the hydrophilic moiety in an ester compound to increase the immunopotentiating activity of the lactic acid bacteria. Therefore, examination of the hydrophobic moiety was conducted next.

Method

Figure 3:
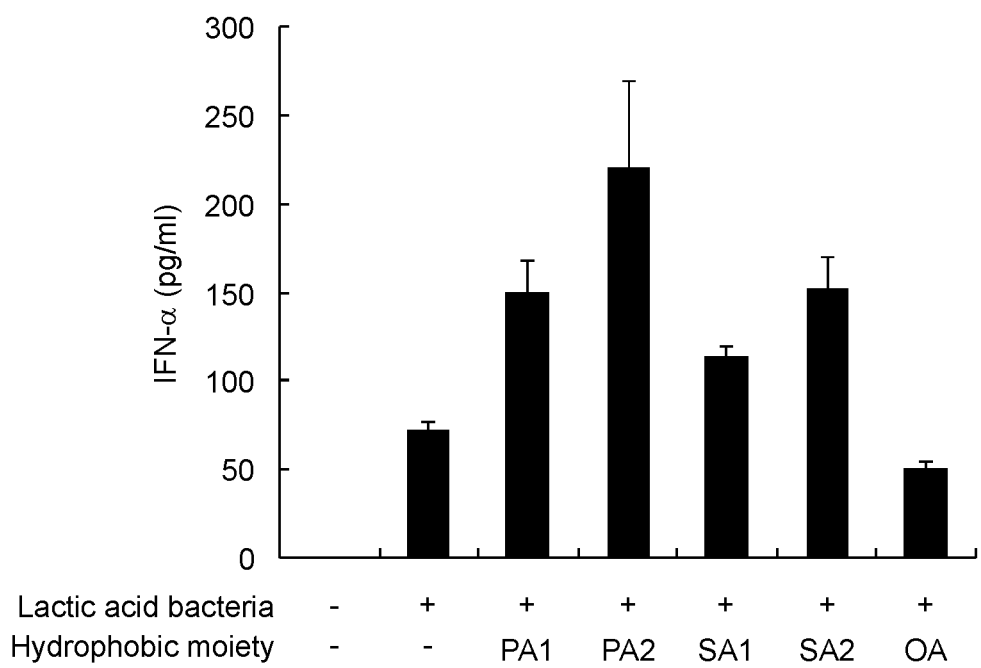
FIG. 3 illustrates the results of a narrowing examination of the type (the hydrophobic moiety) of ester compounds of a polyol and a fatty acid.

To 500 μl of the cell suspension prepared in the method described in Example 1, 5 μl of a mixture of the lactic acid bacteria (the strain JCM5805) and one of the samples indicated in FIG. 3 was added. The resulting mixtures were cultured at 37° C., 5% $CO_2$ in a $CO_2$ incubator. The mixtures of the lactic acid bacteria and one of the samples indicated in the figure contained 0.1 (w/v) % of the lactic acid bacteria and 0.25 (w/v) % of one of the samples. The samples were the lactic acid bacteria only, Ryoto Sugar Ester P-1570 (mainly containing sucrose palmitate) (PA1) (Mitsubishi-Kagaku Foods Corporation), Ryoto Sugar Ester P-1670 (mainly containing sucrose palmitate) (PA2) (Mitsubishi-Kagaku Foods Corporation), Ryoto Sugar Ester S-1570 (mainly containing sucrose stearate) (SA1) (Mitsubishi-Kagaku Foods Corporation), Ryoto Sugar Ester S-1670 (mainly containing sucrose stearate) (SA2) (Mitsubishi-Kagaku Foods Corporation), and Ryoto Sugar Ester O-1570 (mainly containing sucrose oleate) (OA) (Mitsubishi-Kagaku Foods Corporation). Culture supernatants were collected 24 hours later and the concentration of interferon-α was measured by interferon-α assay kit (Pestka Biomedical Laboratories, Inc). Accordingly, examination of the hydrophobic moiety was conducted by using ester compounds containing sucrose as the unified hydrophilic moiety and a variety of fatty acids: palmitic acid (saturated fatty acid), stearic acid (saturated fatty acid), and oleic acid (unsaturated fatty acid) as the hydrophobic moiety.

Result

Results are illustrated in FIG. 3. 0.1% JCM5805 alone exhibits the interferon-α inducing activity and the interferon-α inducing activity was increased by the ester compounds containing a saturated fatty acid, stearic acid or palmitic acid as the hydrophobic moiety and the interferon-α inducing activity was weakened by the ester compound containing an unsaturated fatty acid, oleic acid. Accordingly, it was indicated that a saturated fatty acid is appropriate for the hydrophobic moiety in an ester compound to increase the immunopotentiating activity of lactic acid bacteria.

Example 4 Examination of Type of Ester Compound of Polyol and Fatty Acid

To examine ester compounds to increase the immunopotentiating activity of lactic acid bacteria in detail, evaluation of ester compounds of a fatty acid and a polyol was conducted by using single components, monoglycerol myristate, monoglycerol palmitate, and monoglycerol stearate.

Method

Figure 4:
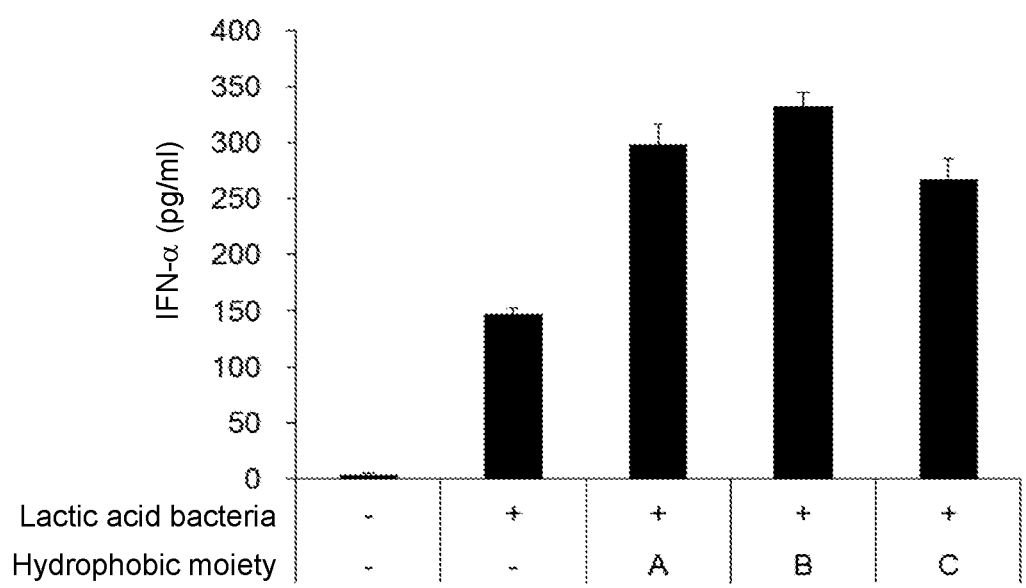
FIG. 4 illustrates the results of an examination of the type of ester compounds of a polyol and a fatty acid.

To 500 μl of the cell suspension prepared in the method described in Example 1, 5 μl of a mixture of the lactic acid bacteria (the strain JCM5805) and one of the samples indicated in FIG. 4 was added. The resulting mixtures were cultured at 37° C., 5% $CO_2$ in a $CO_2$ incubator. The mixtures of the lactic acid bacteria and one of the samples indicated in the figure contained 0.1 (w/v) % of the lactic acid bacteria and 0.25 (w/v) % of one of the fatty acid esters of monoglycerol. The samples were the lactic acid bacteria only, monoglycerol myristate, monoglycerol palmitate, and monoglycerol stearate. Culture supernatants were collected 24 hours later and the concentration of interferon-α was measured by interferon-α assay kit (Pestka Biomedical Laboratories, Inc). Accordingly, examination of ester single components having glycerol as the hydrophilic moiety and myristic acid, palmitic acid, and stearic acid as the hydrophobic moiety was conducted.

Result

Results are illustrated in FIG. 4. 0.1% JCM5805 alone exhibits the interferon-α inducing activity and the interferon-α inducing activity was further increased by the fatty acid esters of monoglycerol containing myristic acid, palmitic acid, and stearic acid in the hydrophobic moiety. Accordingly, it was indicated that even ester compound single components having glycerol as the hydrophilic moiety and a saturated fatty acid as the hydrophobic moiety increase the immunopotentiating activity of lactic acid bacteria.

Example 5 Examination 2 of Type of Ester Compound of Polyol and Fatty Acid

To examine ester compounds to increase the immunopotentiating activity of lactic acid bacteria in detail, evaluation of ester compounds of a fatty acid and a polyol was conducted by using a single component, sucrose palmitate.

Method

Myeloblasts were collected from female 129/SV mice according to a usual method and erythrocytes were removed. The obtained myeloblasts were suspended at $5 \times 10^5$ cells/ml in RPMI medium (Sigma-Aldrich Co. LLC) containing 10% FBS, 50 μM β-mercaptoethanol, and 100 ng/ml Flt-3L. Medium was inoculated with 1 ml of the obtained cell suspension and the culture was incubated at 37° C., 5% $CO_2$ in a $CO_2$ incubator for 1 week to induce dendritic cells. After the 1 week of culturing, 10 μl of a mixture of the lactic acid bacteria (the strain JCM5805) and one of the samples indicated in FIG. 5 was added to 1 ml of the inoculated cell culture. The mixtures of the lactic acid bacteria and one of the samples indicated in FIG. 5 contained 0.1 (w/v) % of the lactic acid bacteria and 0.25 (w/v) % of one of the samples. The samples were the lactic acid bacteria only, sucrose palmitate, and Ryoto Sugar Ester P1670 (mainly containing sucrose palmitate) (Mitsubishi-Kagaku Foods Corporation). Culture supernatants were collected 24 hours later and the concentration of interferon-α was measured by interferon-α assay kit (Pestka Biomedical Laboratories, Inc).

Result

Figure 5:
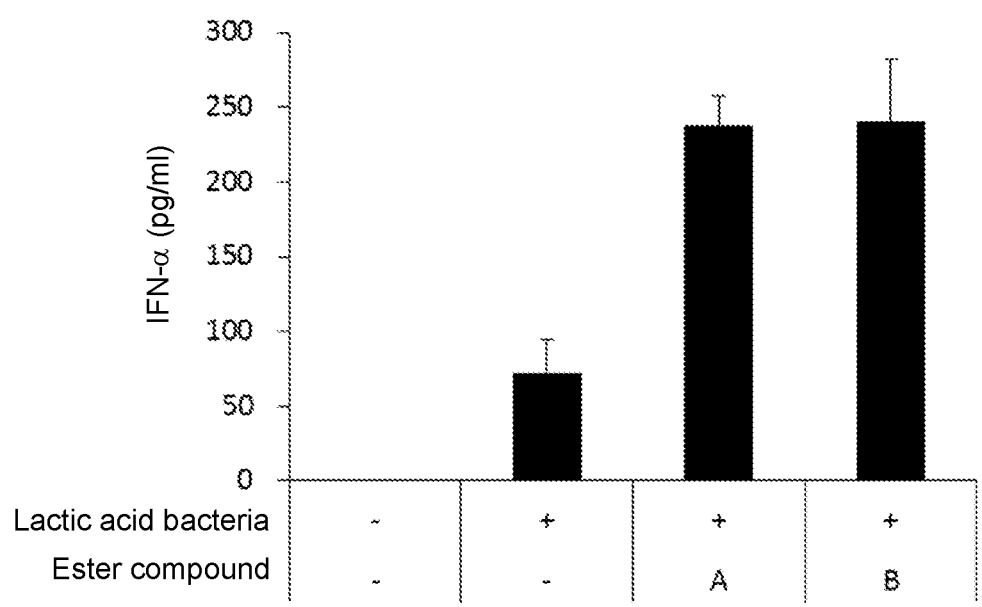
FIG. 5 illustrates the results of Examination 2 of the type of ester compounds of a polyol and a fatty acid.

Results are illustrated in FIG. 5. 0.1% JCM5805 alone exhibits the interferon-α inducing activity and the interferon-α inducing activity was increased by sucrose palmitate to the similar level to that by Ryoto Sugar Ester P1670. Accordingly, it was indicated that even an ester compound single component having sucrose as the hydrophilic moiety and a saturated fatty acid as the hydrophobic moiety increases the immunopotentiating activity of lactic acid bacteria.

Example 6 Examination of Organic Acid Modification of Ester Compound of Polyol and Fatty Acid It was confirmed that a polyol is appropriate for the hydrophilic moiety and a saturated fatty acid is appropriate for the hydrophobic moiety in an ester compound to increase the immunopotentiating activity of lactic acid bacteria. Therefore, examination of effect of the presence or absence of the organic acid modification in the polyol moiety of the ester compound was conducted next.
(1) When lactic acid bacterial concentration is 0.1%

Method

Figure 6:
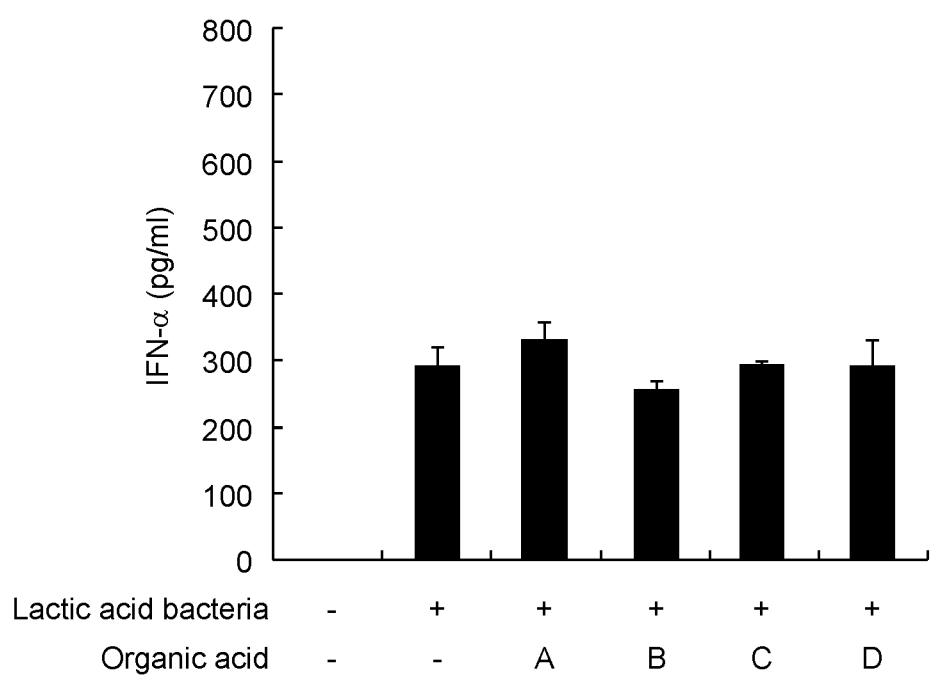
FIG. 6 illustrates the results of an examination of the modification of ester compounds of a polyol and a fatty acid with organic acids (the lactic acid bacterial concentration is 0.1%).

To 500 µl of the cell suspension prepared in the method described in Example 1, 5 µl of a mixture of the lactic acid bacteria (the strain JCM5805) and one of the samples indicated in FIG. 6 was added. The resulting mixtures were cultured at 37° C., 5% $CO_2$ in a $CO_2$ incubator. The mixtures of the lactic acid bacteria and one of the samples indicated in the figure contained 0.1 (w/v) % of the lactic acid bacteria and 0.25 (w/v) % of one of the samples. The samples were the lactic acid bacteria only, Emulsy P-100 (mainly containing an ester compound of monoglycerol and a saturated fatty acid) (A) (Riken Vitamin Co., Ltd.), Poem W-60 (mainly containing an ester compound of diacetyltartaric monoglyceride and saturated fatty acid) (B) (Riken Vitamin Co., Ltd.), Poem B-15V (mainly containing an ester compound of succinic monogluceride and saturated fatty acid) (C) (Riken Vitamin Co., Ltd.), and Poem BS-20 (mainly containing an ester compound of succinic monoglyceride and saturated fatty acid) (D) (Riken Vitamin Co., Ltd.). Culture supernatants were collected 24 hours later and the concentration of interferon-α was measured by interferon-α assay kit (Pestka Biomedical Laboratories, Inc). Accordingly, examination of the organic acid modification was conducted by using ester compounds having monoglycerol as the unified hydrophilic moiety and a saturated fatty acid as the unified hydrophobic moiety to which tartaric acid or succinic acid was bonded as the organic acid modification.

Result

Results are illustrated in FIG. 6. 0.1% JCM5805 alone exhibits the interferon-α inducing activity and the interferon-α inducing activity was increased by the emulsifier without the organic acid modification, but the IFN-α inducing activity was not increased by the ester compounds modified with tartaric acid and succinic acid. Accordingly, it was indicated that a saturated fatty acid that is not modified with an organic acid is appropriate for the hydrophobic moiety in an ester compound to increase the immunopotentiating activity of lactic acid bacteria, when the lactic acid bacterial concentration is relatively high.
(2) When the lactic acid bacterial concentration is 0.01%

Method

Figure 7:
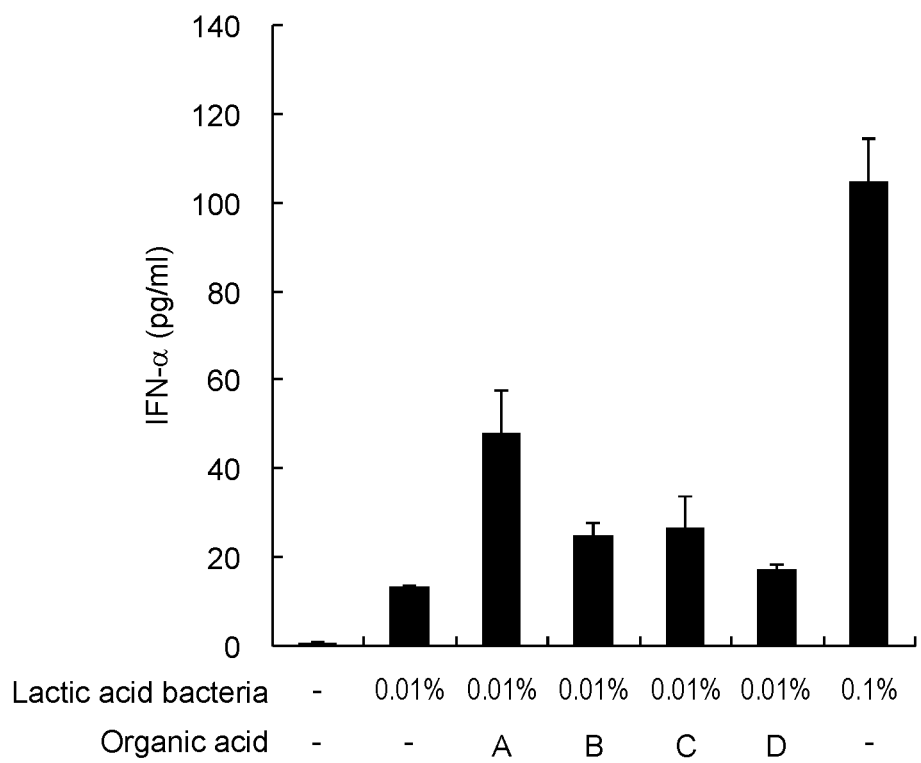
FIG. 7 illustrates the results of an examination of the modification of ester compounds of a polyol and a fatty acid with organic acids (the lactic acid bacterial concentration is 0.01%).

To 500 µA of the cell suspension prepared in the method described in Example 1, 5 µl of a mixture of the lactic acid bacteria (the strain JCM5805) and one of the samples indicated in FIG. 7 was added. The resulting mixtures were cultured at 37° C., 5% $CO_2$ in a $CO_2$ incubator. The mixtures of the lactic acid bacteria and one of the samples indicated in the figure contained 0.01 (w/v) % of the lactic acid bacteria and 0.25 (w/v) % of one of the samples. The samples were the lactic acid bacteria only, Emulsy P-100 (mainly containing an ester compound of monoglycerol and a saturated fatty acid) (A) (Riken Vitamin Co., Ltd.), Poem W-60 (mainly containing an ester compound of diacetyltartaric monoglyceride and saturated fatty acid) (B) (Riken Vitamin Co., Ltd.), Poem B-15V (mainly containing an ester compound of succinic monoglyceride and saturated fatty acid) (C) (Riken Vitamin Co., Ltd.), and Poem BS-20 (mainly containing an ester compound of succinic monoglyceride and saturated fatty acid) (D) (Riken Vitamin Co., Ltd.). Culture supernatants were collected 24 hours later and the concentration of interferon-α was measured by interferon-α assay kit (Pestka Biomedical Laboratories, Inc). Accordingly, examination of the organic acid modification was conducted by using ester compounds having monoglycerol as the unified hydrophilic moiety and a saturated fatty acid as the unified hydrophobic moiety to which tartaric acid or succinic acid was bonded as the organic acid modification.

Result

Results are illustrated in FIG. 7. 0.01% JCM5805 alone exhibits the interferon-α inducing activity and the interferon-α inducing activity is increased by the emulsifier without the organic acid modification. The increase in the inducing activity was smaller with the ester compounds modified with tartaric acid and succinic acid, but a small increase in the activity was observed. Accordingly, it was indicated that a saturated fatty acid is appropriate for the hydrophobic moiety in an ester compound to increase the immunopotentiating activity of lactic acid bacteria and the ester compound is effective with or without the organic acid modification, when the lactic acid bacterial concentration is low.

Example 7 Examination 1 of Concentration Range of Ester Compound of Polyol and Fatty Acid

Method

Figure 8:
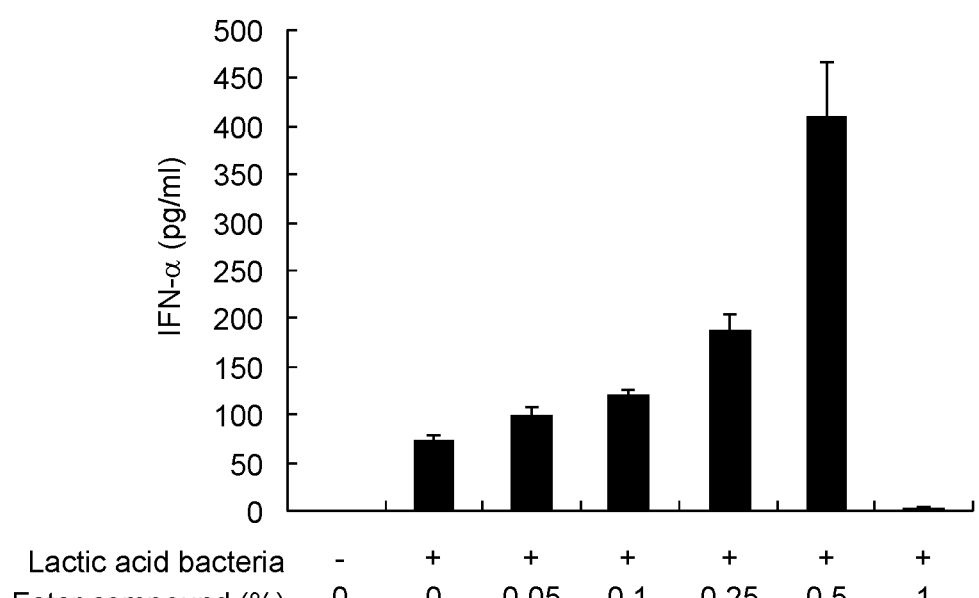
FIG. 8 illustrates the results of an examination of the range of the concentration of an ester compound of a polyol and a fatty acid (the lactic acid bacterial concentration is 0.1%).

To 500 µl of the cell suspension prepared in the method described in Example 1, 5 µl of a mixture of the lactic acid bacteria (the strain JCM5805) and the sample indicated in FIG. 8 was added. The resulting mixtures were cultured at 37° C., 5% $CO_2$ in a $CO_2$ incubator. The mixtures of the lactic acid bacteria and the sample indicated in the figure contained 0.1 (w/v) % of the lactic acid bacteria and 0-1 (w/v) % of the sample. Ryoto Sugar Ester P1670 (mainly containing sucrose palmitate) (Mitsubishi-Kagaku Foods Corporation) was used as the sample. Culture supernatants were collected 24 hours later and the concentration of interferon-α was measured by interferon-α assay kit (Pestka Biomedical Laboratories, Inc). Accordingly, examination of the concentration-dependence on the concentration of Ryoto Sugar Ester P1670, which is an ester compound, in the range from 0.05 (w/v) % to 1 (w/v) % was conducted with a fixed JCM5805 concentration of 0.1 (w/v) %.

Result

Results are illustrated in FIG. 8. 0.1 (w/v) % JCM5805 alone exhibits the interferon-α inducing activity and the interferon-α inducing activity was synergistically increased in a concentration-dependent manner on the concentration of Ryoto Sugar Ester P1670 in the range from 0.05 (w/v) % to 0.5 (w/v) %. Accordingly, the ester compound in the concentration range of 0.5 to 5 relative to the JCM5805 concentration, defined as 1, exhibited the synergistic effect. Reason for the lack of synergistic effect at an ester compound concentration of 1 (w/v) % is considered to be that the high concentration of the ester compound had a damage on the cells.

Figure 9:
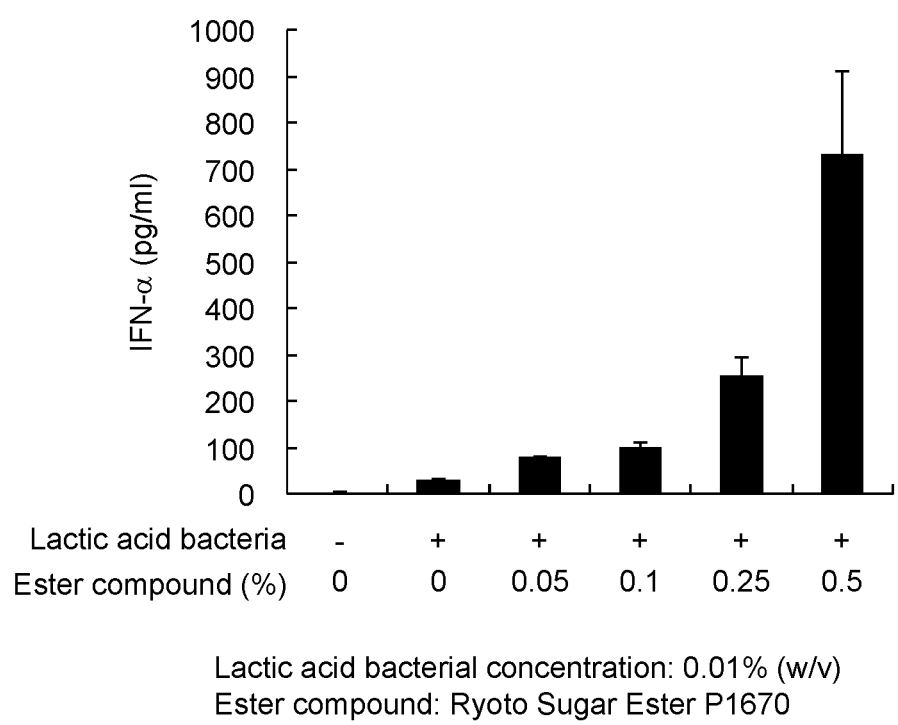
FIG. 9 illustrates results of an examination of the range of the concentration of an ester compound of a polyol and a fatty acid (the lactic acid bacterial concentration is 0.01%).

Example 8 Examination 2 of Concentration Range of Ester Compound of Polyol and Fatty Acid Method To 500 μl of the cell suspension prepared in the method described in Example 1, 5 μl of a mixture of the lactic acid bacteria (the strain JCM5805) and the sample indicated in FIG. 9 was added. The resulting mixtures were cultured at 37° C., 5% $CO_2$ in a $CO_2$ incubator. The mixtures of the lactic acid bacteria and the sample indicated in the figure contained 0.01 (w/v) % of the lactic acid bacteria and 0-0.5 (w/v) % of the sample. Ryoto Sugar Ester P1670 (mainly containing sucrose palmitate) (Mitsubishi-Kagaku Foods Corporation) was used as the sample. Culture supernatants were collected 24 hours later and the concentration of interferon-α was measured by interferon-α assay kit (Pestka Biomedical Laboratories, Inc). Accordingly, examination of the concentration-dependence on the concentration of Ryoto Sugar Ester P1670, which is an ester compound, in the range from 0.05 (w/v) % to 0.5 (w/v) % was conducted with a fixed JCM5805 concentration of 0.01 (w/v) %.

Result

Results are illustrated in FIG. 9. 0.01% JCM5805 alone exhibits the interferon-α inducing activity and Ryoto Sugar Ester P1670 synergistically increased the interferon-α inducing activity in a concentration-dependent manner. The synergistic effect was observed in the ester compound concentration range of 0.05 to 0.5 (w/v) % and the synergistic effect was observed in the ester compound concentration range of 5 to 50 relative to the JCM5805 concentration, defined as 1.

Example 9 Examination of Effect on Lactic Acid Bacteria Other than Strain JCM5805

Method

Figure 10:
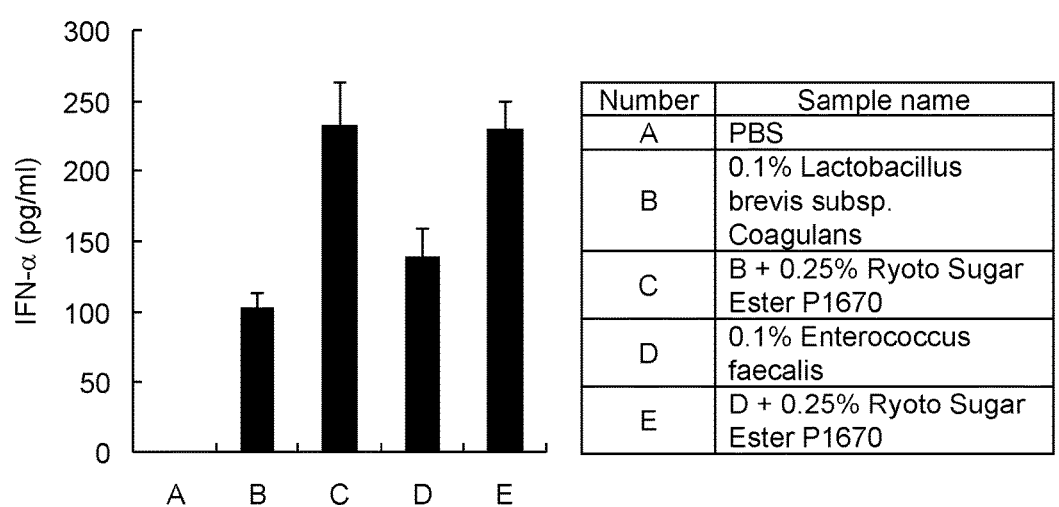
FIG. 10 illustrates results of an examination of the effect on lactic acid bacteria other than the strain JCM5805 (No. 1).

To 500 μl of the cell suspension prepared in the method described in Example 1, 5 μl of a mixture of an lactic acid bacteria and a sample indicated in FIG. 10 was added. The resulting mixtures were cultured at 37° C., 5% $CO_2$ in a $CO_2$ incubator. Culture supernatants were collected 24 hours later and the concentration of interferon-α was measured by interferon-α assay kit (Pestka Biomedical Laboratories, Inc). Accordingly, the effect of an ester compound (Ryoto Sugar Ester P-1670 (sucrose palmitate) (Mitsubishi-Kagaku Foods Corporation)) on the lactic acid bacteria *Enterococcus faecalis* and *Lactobacillus brevis* subsp. *coagulans* was examined.

Result

Results are illustrated in FIG. 10. *Enterococcus faecalis* or *Lactobacillus brevis* subsp. *coagulans* alone exhibited the interferon-α inducing activity (D and B in FIG. 10) and the interferon-α inducing activity was increased by Ryoto Sugar Ester P-1670 (E and C in FIG. 10). This indicates that lactic acid bacteria whose immunopotentiating activity is increased by an ester compound of a polyol and a fatty acid are not limited to the strain JCM5805.

INDUSTRIAL APPLICABILITY

Lactic acid bacterial immunopotentiating activity-increasing agents that are ester compounds of a polyol and a saturated fatty acid according to the present invention increase the immunopotentiating activity of lactic acid bacteria used in medicines and beverages and foods.

All publications, patents, and patent applications cited herein are incorporated herein by reference as their entireties.

The invention claimed is:

1. A composition comprising lactic acid bacteria having immunopotentiating activity and a lactic acid bacterial immunopotentiating activity-increasing composition comprising an ester compound of a polyol and a saturated fatty acid as an active ingredient, wherein the ratio of the concentration of the ester compound of the polyol and the saturated fatty acid to the concentration of the lactic acid bacteria having the immunopotentiating activity is in the range of 0.5 to 50:1 and wherein the concentration of the ester compound is in the range of 0.05 to 0.5% (w/v), and the lactic acid bacteria having the immunopotentiating activity are of *Lactococcus lactis* JCM5805 strain.

2. The composition according to claim 1, wherein the immunopotentiating activity of the lactic acid bacteria having the immunopotentiating activity is increased compared to the immunopotentiating activity of the lactic acid bacteria which are not contacted with the ester compound of the polyol and the saturated fatty acid.

3. The composition according to claim 1, wherein the composition is a beverage or food.

4. The composition according to claim 1, wherein the polyol is selected from the group consisting of monoglycerol, polyglycerol, and sucrose.

5. The composition according to claim 1, wherein the saturated fatty acid is selected from the group consisting of caprylic acid, capric acid, lauric acid, myristic acid, palmitic acid, stearic acid, and behenic acid.

6. The composition according to claim 1, wherein the ester compound of the polyol and the saturated fatty acid is not modified with any organic acid.

7. The composition according to claim 1, wherein the lactic acid bacteria having the immunopotentiating activity induce interferon production of an interferon-producing cell.

8. A method of increasing immunopotentiating activity of lactic acid bacteria having immunopotentiating activity, comprising contacting the lactic acid bacteria having immunopotentiating activity with a lactic acid bacterial immunopotentiating activity-increasing composition comprising an ester compound of a polyol and a saturated fatty acid as an active ingredient, wherein the ratio of the concentration of the ester compound of the polyol and the saturated fatty acid to the concentration of the lactic acid bacteria having the immunopotentiating activity is in the range of 0.5 to 50:1 and wherein the concentration of the ester compound is in the range of 0.05 to 0.5% (w/v), and the lactic acid bacteria having the immunopotentiating activity are of *Lactococcus lactis* JCM5805 strain, and wherein the immunopotentiating activity of the lactic acid bacteria contacted with the ester compound of the polyol and the saturated fatty acid is increased compared to the immunopotentaiting activity of the lactic acid bacteria which are not contacted with the ester compound of the polyol and the saturated fatty acid.

9. The method according to claim 8, wherein the polyol is selected from the group consisting of monoglycerol, polyglycerol, and sucrose.

10. The method according to claim 8, wherein the saturated fatty acid is selected from the group consisting of caprylic acid, capric acid, lauric acid, myristic acid, palmitic acid, stearic acid and behenic acid.

11. The method according to claim 8, wherein the ester compound of the polyol and the saturated fatty acid is not modified with any organic acid.

12. The method according to claim 8, wherein the lactic acid bacteria having the immunopotentiating activity induce interferon production of an interferon-producing cell.

13. The method of claim 8, wherein the contacting is by culturing the lactic acid bacteria having the immunopotentiating activity in the presence of the lactic acid bacterial immunopotentiating activity-increasing composition.

14. The method of claim 8, wherein the contacting is by adding the lactic acid bacterial immunopotentiating activity-increasing composition to a liquid containing the lactic acid bacteria having the immunopotentiating activity.

\* \* \* \* \*